(12) United States Patent
Li et al.

(10) Patent No.: US 7,132,284 B2
(45) Date of Patent: Nov. 7, 2006

(54) ADENOVIRUS PACKAGING CELL LINES

(75) Inventors: Yuanhao Li, Palo Alto, CA (US);
Deborah Farson, Belmont, CA (US);
Luqun Tao, Foster City, CA (US);
DeChao Yu, Foster City, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 0 days.

(21) Appl. No.: 11/240,406

(22) Filed: Oct. 3, 2005

(65) Prior Publication Data

US 2006/0024829 A1 Feb. 2, 2006

Related U.S. Application Data

(63) Continuation of application No. 10/613,106, filed on Jul. 3, 2003, now Pat. No. 7,026,164.

(51) Int. Cl.
*C12N 15/63* (2006.01)
*C12N 15/64* (2006.01)
*C12N 15/861* (2006.01)
*C12N 7/01* (2006.01)
*C12N 5/10* (2006.01)
*A61K 48/00* (2006.01)

(52) U.S. Cl. .................... 435/371; 435/320.1; 435/325; 435/366; 435/235.1

(58) Field of Classification Search ...................... None
See application file for complete search history.

(56) References Cited

U.S. PATENT DOCUMENTS

| | | | |
|---|---|---|---|
| 5,891,690 A | 4/1999 | Massie | |
| 5,994,128 A | 11/1999 | Fallaux et al. | |
| 6,265,212 B1 | 7/2001 | Fallaux et al. | |
| 6,420,120 B1 * | 7/2002 | Boulanger et al. | 435/7.1 |
| 6,869,936 B1 * | 3/2005 | Vogels et al. | 514/44 |
| 2001/0049136 A1 | 12/2001 | Imler et al. | |
| 2005/0003506 A1 | 1/2005 | Li et al. | |
| 2005/0003545 A1 | 1/2005 | Li et al. | |
| 2005/0095705 A1 | 5/2005 | Kadan et al. | |

FOREIGN PATENT DOCUMENTS

| | | |
|---|---|---|
| WO | WO 95/34671 | 6/1995 |
| WO | WO 96/17053 | 11/1995 |
| WO | WO 96/18418 | 12/1995 |

OTHER PUBLICATIONS

Gorziglia, et al., "Elimination of both E1 and E2a from Adenovirus Vectors Further Improves Prospects for In Vivo Human Gene Therapy", Journal of Virology, vol. 70, No. 6, pp. 4173-4178, 1996.
Murakami, et al., "A Single Short Stretch of Homology Between Adenoviral Vector and Packaging Cell Line Can Give Rise to Cytopathic Effect-Inducing, Helper-Dependent E1-Positive Particles", Human Gene Therapy, vol. 13, pp. 909-920, 2002.
Louis, et al., "Cloning and Sequencing of the Cellular-Viral Junctions from the Human Adenovirus Type 5 Transformed 293 Cell Line", Virology, vol. 233, pp. 423-429, 1997.
Hehir, et al., "Molecular Characterization of Replication-Competent Variants of Adenovirus Vectors and Genome Modifications To Prevent Their Occurrence", Journal of Virology, vol. 70, No. 12, pp. 8459-8467, 1996.
Berkner, et al., "Development of Adenovirus Vectors for he Expression of Heterologous Genes", Biotechniques, vol. 6, pp. 616-629, 1988.
Fallaux, et al., "Net Helper Cells and Matched Early Region 1-Deleted Adenovirus Vectors Prevent Generation of Replication-Component Adenoviruses", Human Gene Therapy, vol. 9, pp. 1909-1917, 1998.
Graham, et al., "Characteristics of a Human Cell Line Transformed by DNA from Human Adenovirus Type 5", J. General Virology, vol. 36, pp. 59-72, 1977.
Kim, et al., "Development of a packaging cell line for propagation of replication-deficient adenovirus vector", Exp. Mol. Med., vol. 33, No. 3, pp. 145-149, 2001.
Kozarsky, et al., "Gene therapy: adenovirus vectors", Curr. Opin. Genet. Dev., vol. 3, pp. 499-503, 1993.
Schiedner, et al., "Efficient Transformation of Primary Human Amniocytes by E1 Functions of Ad5: Generation of New Cell Lines for Adenoviral Vector Production", Human Gene Therapy, vol. 11, pp. 2105-2116, 2000.
Yu, et al., "Selectively replicating oncolytic adenoviruses as cancer therapeutics", Curr. Opin. Mol. Ther., vol. 4, No. 5, pp. 435-443, 2002.

* cited by examiner

*Primary Examiner*—David Guzo
(74) *Attorney, Agent, or Firm*—DLA Piper US LLP

(57) ABSTRACT

Adenovirus packaging cell lines for growth of an E1A/E1B deficient adenovirus that is substantially free of replication competent adenovirus (RCA) are provided. Methods for producing adenovirus substantially free of RCA are also provided, wherein the adenovirus is grown in a cell line containing coding sequences for adenovirus E1A and E1B, which are operably linked to promoters that lack polynucleotide sequences sharing substantial sequence identity with the native adenovirus E1A and E1B promoters.

23 Claims, 4 Drawing Sheets

SEQUENCE LISTING

<160> NUMBER OF SEQ ID NOS: 8

<210> SEQ ID NO 1
<211> LENGTH: 986
<212> TYPE: DNA
<213> ORGANISM: adenovirus

<400> SEQUENCE: 1

```
atgagacata ttatctgcca cggaggtgtt attaccgaag aaatggccgc cagtcttttg      60
gaccagctga tcgaagaggt actggctgat aatcttccac ctcctagcca ttttgaacca     120
cctacccttc acgaactgta tgatttagac gtgacggccc ccgaagatcc caacgaggag     180
gcggtttcgc agattttttcc cgactctgta atgttggcgg tgcaggaagg gattgactta     240
ctcacttttc cgccggcgcc cggttctccg gagccgcctc acctttcccg gcagcccgag     300
cagccggagc agagagcctt gggtccggtt tctatgccaa accttgtacc ggaggtgatc     360
gatcttacct gccacgaggc tggctttcca cccagtgacg acgaggatga agagggtgag     420
gagtttgtgt tagattatgt ggagcacccc gggcacggtt gcaggtcttg tcattatcac     480
cggaggaata cggggggaccc agatattatg tgttcgcttt gctatatgag gacctgtggc     540
atgtttgtct acagtaagtg aaaattatgg gcagtgggtg atagagtggt gggtttggtg     600
tggtaatttt tttttaatt tttacagttt tgtggtttaa agaattttgt attgtgattt     660
```

-continued

```
ttttaaaagg tcctgtgtct gaacctgagc ctgagcccga gccagaaccg gagcctgcaa      720
gacctacccg ccgtcctaaa atggcgcctg ctatcctgag acgcccgaca tcacctgtgt      780
ctagagaatg caatagtagt acggatagct gtgactccgg tccttctaac acacctcctg     840
agatacaccc ggtggtcccg ctgtgcccca ttaaaccagt tgccgtgaga gttggtgggc      900
gtcgccaggc tgtggaatgt atcgaggact tgcttaacga gcctgggcaa cctttggact      960
tgagctgtaa acgccccagg ccataa                                            986
```

<210> SEQ ID NO 2
<211> LENGTH: 289
<212> TYPE: PRT
<213> ORGANISM: adenovirus

<400> SEQUENCE: 2

```
Met Arg His Ile Ile Cys His Gly Gly Val Ile Thr Glu Glu Met Ala
  1               5                  10                  15

Ala Ser Leu Leu Asp Gln Leu Ile Glu Glu Val Leu Ala Asp Asn Leu
             20                  25                  30

Pro Pro Pro Ser His Phe Glu Pro Pro Thr Leu His Glu Leu Tyr Asp
         35                  40                  45

Leu Asp Val Thr Ala Pro Glu Asp Pro Asn Glu Glu Ala Val Ser Gln
 50                  55                  60

Ile Phe Pro Asp Ser Val Met Leu Ala Val Gln Glu Gly Ile Asp Leu
 65                  70                  75                  80

Leu Thr Phe Pro Pro Ala Pro Gly Ser Pro Glu Pro Pro His Leu Ser
                 85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
        115                 120                 125

Phe Pro Pro Ser Asp Asp Glu Asp Glu Glu Gly Glu Glu Phe Val Leu
130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165                 170                 175

Arg Thr Cys Gly Met Phe Val Tyr Ser Pro Val Ser Glu Pro Glu Pro
            180                 185                 190

Glu Pro Glu Pro Glu Pro Ala Arg Pro Thr Arg Arg Pro Lys
        195                 200                 205

Met Ala Pro Ala Ile Leu Arg Arg Pro Thr Ser Pro Val Ser Arg Glu
    210                 215                 220

Cys Asn Ser Ser Thr Asp Ser Cys Asp Ser Gly Pro Ser Asn Thr Pro
225                 230                 235                 240

Pro Glu Ile His Pro Val Val Pro Leu Cys Pro Ile Lys Pro Val Ala
                245                 250                 255

Val Arg Val Gly Gly Arg Arg Gln Ala Val Glu Cys Ile Glu Asp Leu
            260                 265                 270

Leu Asn Glu Pro Gly Gln Pro Leu Asp Leu Ser Cys Lys Arg Pro Arg
        275                 280                 285

Pro
```

<210> SEQ ID NO 3

-continued

<211> LENGTH: 243
<212> TYPE: PRT
<213> ORGANISM: adenovirus

<400> SEQUENCE: 3

```
Met Arg His Ile Ile Cys His Gly Gly Val Ile Thr Glu Glu Met Ala
  1               5                  10                  15

Ala Ser Leu Leu Asp Gln Leu Ile Glu Glu Val Leu Ala Asp Asn Leu
             20                  25                  30

Pro Pro Pro Ser His Phe Glu Pro Thr Leu His Glu Leu Tyr Asp
         35                  40                  45

Leu Asp Val Thr Ala Pro Glu Asp Pro Asn Glu Glu Ala Val Ser Gln
 50                  55                  60

Ile Phe Pro Asp Ser Val Met Leu Ala Val Gln Glu Gly Ile Asp Leu
 65                  70                  75                  80

Leu Thr Phe Pro Pro Ala Pro Gly Ser Pro Glu Pro His Leu Ser
             85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
            115                 120                 125

Phe Pro Pro Ser Asp Asp Glu Asp Glu Glu Gly Pro Val Ser Glu Pro
130                 135                 140

Glu Pro Glu Pro Glu Pro Glu Pro Ala Arg Pro Thr Arg Arg
145                 150                 155                 160

Pro Lys Met Ala Pro Ala Ile Leu Arg Arg Pro Thr Ser Pro Val Ser
            165                 170                 175

Arg Glu Cys Asn Ser Ser Thr Asp Ser Cys Asp Ser Gly Pro Ser Asn
            180                 185                 190

Thr Pro Pro Glu Ile His Pro Val Val Pro Leu Cys Pro Ile Lys Pro
            195                 200                 205

Val Ala Val Arg Val Gly Gly Arg Arg Gln Ala Val Glu Cys Ile Glu
210                 215                 220

Asp Leu Leu Asn Glu Pro Gly Gln Pro Leu Asp Leu Ser Cys Lys Arg
225                 230                 235                 240

Pro Arg Pro
```

<210> SEQ ID NO 4
<211> LENGTH: 2144
<212> TYPE: DNA
<213> ORGANISM: Adenovirus

<400> SEQUENCE: 4

```
gccgtgggct aatcttggtt acatctgacc tcatggaggc ttgggagtgt ttggaagatt     60
tttctgctgt gcgtaacttg ctggaacaga gctctaacag tacctcttgg ttttggaggt    120
ttctgtgggg ctcatcccag gcaaagttag tctgcagaat taaggaggat tacaagtggg    180
aatttgaaga gcttttgaaa tcctgtggtg agctgtttga ttctttgaat ctgggtcacc    240
aggcgctttt ccaagagaag gtcatcaaga ctttggattt ttccacaccg gggcgcgctg    300
cggctgctgt tgcttttttg agttttataa aggataaatg gagcgaagaa acccatctga    360 gcgggggta cctgctggat tttctggcca tgcatctgtg gagagcggtt gtgagacaca    420
agaatcgcct gctactgttg tcttccgtcc gcccggcgat aataccgacg gaggagcagc    480
agcagcagca ggaggaagcc aggcggcggc ggcaggagca gagcccatgg aacccgagag    540
```

-continued

```
ccggcctgga ccctcgggaa tgaatgttgt acaggtggct gaactgtatc cagaactgag    600
acgcattttg acaattacag aggatgggca ggggctaaag ggggtaaaga gggagcgggg    660
ggcttgtgag gctacagagg aggctaggaa tctagctttt agcttaatga ccagacaccg    720
tcctgagtgt attactttc aacagatcaa ggataattgc gctaatgagc ttgatctgct     780
ggcgcagaag tattccatag agcagctgac cacttactgg ctgcagccag gggatgattt    840
tgaggaggct attagggtat atgcaaaggt ggcacttagg ccagattgca agtacaagat    900
cagcaaactt gtaaatatca ggaattgttg ctacatttct gggaacgggg ccgaggtgga    960
gatagatacg gaggataggg tggcctttag atgtagcatg ataaatatgt ggccgggggt   1020
gcttggcatg gacggggtgg ttattatgaa tgtaaggttt actggcccca attttagcgg   1080
tacggttttc ctggccaata ccaaccttat cctacacggt gtaagcttct atgggtttaa   1140
caatacctgt gtggaagcct ggaccgatgt aagggttcgg ggctgtgcct tttactgctg   1200
ctggaagggg gtggtgtgtc gccccaaaag cagggcttca attaagaaat gcctctttga   1260
aaggtgtacc ttgggtatcc tgtctgaggg taactccagg gtgcgccaca atgtggcctc   1320
cgactgtggt tgcttcatgc tagtgaaaag cgtggctgtg attaagcata acatggtatg   1380
tggcaactgc gaggacaggg cctctcagat gctgacctgc tcggacggca actgtcacct   1440
gctgaagacc attcacgtag ccagccactc tcgcaaggcc tggccagtgt ttgagcataa   1500
catactgacc cgctgttcct tgcatttggg taacaggagg ggggtgttcc taccttacca   1560
atgcaatttg agtcacacta agatattgct tgagcccgag agcatgtcca aggtgaacct   1620
gaacggggtg tttgacatga ccatgaagat ctggaaggtg ctgaggtacg atgagacccg   1680
caccaggtgc agaccctgcg agtgtggcgg taaacatatt aggaaccagc ctgtgatgct   1740
ggatgtgacc gaggagctga ggcccgatca cttggtgctg gcctgcaccc gcgctgagtt   1800
tggctctagc gatgaagata cagattgagg tactgaaatg tgtgggcgtg gcttaagggt   1860
gggaaagaat atataaggtg ggggtcttat gtagttttgt atctgttttg cagcagccgc   1920
cgccgccatg agcaccaact cgtttgatgg aagcattgtg agctcatatt tgacaacgcg   1980
catgccccca tgggccgggg tgcgtcagaa tgtgatgggc tccagcattg atggtcgccc   2040
cgtcctgccc gcaaactcta ctaccttgac ctacgagacc gtgtctggaa cgccgttgga   2100
gactgcagcc tccgccgccg cttcagccgc tgcagccacc gccc                    2144
```

<210> SEQ ID NO 5
<211> LENGTH: 176
<212> TYPE: PRT
<213> ORGANISM: adenovirus

<400> SEQUENCE: 5

```
Met Glu Ala Trp Glu Cys Leu Glu Asp Phe Ser Ala Val Arg Asn Leu
  1               5                  10                  15

Leu Glu Gln Ser Ser Asn Ser Thr Ser Trp Phe Trp Arg Phe Leu Trp
             20                  25                  30

Gly Ser Ser Gln Ala Lys Leu Val Cys Arg Ile Lys Glu Asp Tyr Lys
         35                  40                  45

Trp Glu Phe Glu Glu Leu Leu Lys Ser Cys Gly Glu Leu Phe Asp Ser
     50                  55                  60

Leu Asn Leu Gly His Gln Ala Leu Phe Gln Glu Lys Val Ile Lys Thr
 65                  70                  75                  80

Leu Asp Phe Ser Thr Pro Gly Arg Ala Ala Ala Val Ala Phe Leu
                 85                  90                  95
```

```
Ser Phe Ile Lys Asp Lys Trp Ser Glu Glu Thr His Leu Ser Gly Gly
                100                 105                 110

Tyr Leu Leu Asp Phe Leu Ala Met His Leu Trp Arg Ala Val Val Arg
            115                 120                 125

His Lys Asn Arg Leu Leu Leu Ser Ser Val Arg Pro Ala Ile Ile
        130                 135                 140

Pro Thr Glu Glu Gln Gln Gln Gln Glu Ala Arg Arg Arg
145                 150                 155                 160

Gln Glu Gln Ser Pro Trp Asn Pro Arg Ala Gly Leu Asp Pro Arg Glu
                165                 170                 175

<210> SEQ ID NO 6
<211> LENGTH: 496
<212> TYPE: PRT
<213> ORGANISM: adenovirus

<400> SEQUENCE: 6

Met Glu Arg Arg Asn Pro Ser Glu Arg Gly Val Pro Ala Gly Phe Ser
  1               5                  10                  15

Gly His Ala Ser Val Glu Ser Gly Cys Glu Thr Gln Glu Ser Pro Ala
             20                  25                  30

Thr Val Val Phe Arg Pro Pro Gly Asp Asn Thr Asp Gly Gly Ala Ala
         35                  40                  45

Ala Ala Ala Gly Gly Ser Gln Ala Ala Ala Gly Ala Glu Pro Met
 50                  55                  60

Glu Pro Glu Ser Arg Pro Gly Pro Ser Gly Met Asn Val Val Gln Val
 65                  70                  75                  80

Ala Glu Leu Tyr Pro Glu Leu Arg Arg Ile Leu Thr Ile Thr Glu Asp
                 85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270

Glu Ala Trp Thr Asp Val Arg Val Arg Gly Cys Ala Phe Tyr Cys Cys
        275                 280                 285

Trp Lys Gly Val Val Cys Arg Pro Lys Ser Arg Ala Ser Ile Lys Lys
```

```
                290                 295                 300
Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
                340                 345                 350

Asp Arg Ala Ser Gln Met Leu Thr Cys Ser Asp Gly Asn Cys His Leu
                355                 360                 365

Leu Lys Thr Ile His Val Ala Ser His Ser Arg Lys Ala Trp Pro Val
370                 375                 380

Phe Glu His Asn Ile Leu Thr Arg Cys Ser Leu His Leu Gly Asn Arg
385                 390                 395                 400

Arg Gly Val Phe Leu Pro Tyr Gln Cys Asn Leu Ser His Thr Lys Ile
                405                 410                 415

Leu Leu Glu Pro Glu Ser Met Ser Lys Val Asn Leu Asn Gly Val Phe
                420                 425                 430

Asp Met Thr Met Lys Ile Trp Lys Val Leu Arg Tyr Asp Glu Thr Arg
                435                 440                 445

Thr Arg Cys Arg Pro Cys Glu Cys Gly Gly Lys His Ile Arg Asn Gln
                450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495

<210> SEQ ID NO 7
<211> LENGTH: 873
<212> TYPE: DNA
<213> ORGANISM: Adenovirus

<400> SEQUENCE: 7
atgagacata ttatctgcca cggaggtgtt attaccgaag aaatggccgc cagtcttttg      60
gaccagctga tcgaagaggt actggctgat aatcttccac ctcctagcca ttttgaacca     120
cctacccttc acgaactgta tgatttagac gtgacggccc ccgaagatcc caacgaggag     180
gcggtttcgc agattttttcc cgactctgta atgttggcgg tgcaggaagg gattgactta    240 ctcactttc cgccggcgcc cggttctccg gagccgcctc accttttccg gcagcccgag      300
cagccggagc agagagcctt gggtccggtt tctatgccaa accttgtacc ggaggtgatc     360
gatcttacct gccacgaggc tggctttcca cccagtgacg acgaggatga agagggtgag     420
gagtttgtgt tagattatgt ggagcacccc gggcacggtt gcaggtcttg tcattatcac     480
cggaggaata cggggaccc agatattatg tgttcgcttt gctatatgag gacctgtggc      540
atgtttgtct acagtaagcc tgtgtctgaa cctgagcctg agcccgagcc agaaccggag     600
cctgcaagac ctacccgccg tcctaaaatg gcgcctgcta tcctgagacg cccgacatca     660
cctgtgtcta gagaatgcaa tagtagtacg gatagctgtg actccggtcc ttctaacaca     720
cctcctgaga tacacccggt ggtcccgctg tgccccatta accagttgc cgtgagagtt      780 ggtgggcgtc gccaggctgt ggaatgtatc gaggacttgc ttaacgagcc tgggcaacct     840
ttggacttga gctgtaaacg ccccaggcca taa                                 873

<210> SEQ ID NO 8
<211> LENGTH: 1491
```

<212> TYPE: DNA
<213> ORGANISM: Adenovirus

<400> SEQUENCE: 8

```
atggagcgaa gaaacccatc tgagcggggg gtacctgctg gattttctgg ccatgcatct         60
gtggagagcg gttgtgagac acaagaatcg cctgctactg ttgtcttccg tccgcccggc        120
gataataccg acggaggagc agcagcagca gcaggaggaa gccaggcggc ggcggcagga        180
gcagagccca tggaacccga gagccggcct ggaccctcgg gaatgaatgt tgtacaggtg        240
gctgaactgt atccagaact gagacgcatt ttgacaatta cagaggatgg gcaggggcta        300
aagggggtaa agagggagcg gggggcttgt gaggctacag aggaggctag gaatctagct        360
tttagcttaa tgaccagaca ccgtcctgag tgtattactt ttcaacagat caaggataat        420
tgcgctaatg agcttgatct gctggcgcag aagtattcca tagagcagct gaccacttac        480
tggctgcagc caggggatga ttttgaggag gctattaggg tatatgcaaa ggtggcactt        540
aggccagatt gcaagtacaa gatcagcaaa cttgtaaata tcaggaattg ttgctacatt        600
tctgggaacg gggccgaggt ggagatagat acggaggata gggtggcctt tagatgtagc        660
atgataaata tgtggccggg ggtgcttggc atggacgggg tggttattat gaatgtaagg        720
tttactggcc ccaattttag cggtacggtt ttcctggcca ataccaacct tatcctacac        780
ggtgtaagct tctatgggtt taacaatacc tgtgtggaag cctggaccga tgtaagggtt        840
cggggctgtg cctttactg ctgctggaag ggggtggtgt gtcgcccaa aagcagggct          900
tcaattaaga aatgcctctt tgaaaggtgt accttggta tcctgtctga gggtaactcc         960
agggtgcgcc acaatgtggc ctccgactgt ggttgcttca tgctagtgaa aagcgtggct       1020
gtgattaagc ataacatggt atgtggcaac tgcgaggaca gggcctctca gatgctgacc       1080
tgctcggacg gcaactgtca cctgctgaag accattcacg tagccagcca ctctcgcaag       1140
gcctggccag tgtttgagca taacatactg acccgctgtt ccttgcattt gggtaacagg       1200
aggggggtgt tcctaccta ccaatgcaat ttgagtcaca ctaagatatt gcttgagccc       1260
gagagcatgt ccaaggtgaa cctgaacggg gtgtttgaca tgaccatgaa gatctggaag       1320
gtgctgaggt acgatgagac ccgcaccagg tgcagaccct gcgagtgtgg cggtaaacat       1380
attaggaacc agcctgtgat gctggatgtg accgaggagc tgaggcccga tcacttggtg       1440
ctggcctgca cccgcgctga gtttggctct agcgatgaag atacagattg a                1491
```

ADENOVIRUS PACKAGING CELL LINES

This application is a continuation of U.S. patent application Ser. No. 10/613,106, filed Jul. 3, 2003 now U.S. Pat. No. 7,026,164.

FIELD OF THE INVENTION

The invention relates to novel packaging cell lines useful for the production of recombinant adenoviral vectors, including replication competent adenoviral vectors, oncolytic adenoviral vectors, and replication defective adenoviral vectors with E1 early gene region deletions.

BACKGROUND

Adenoviral (Ad) vectors are highly efficient vehicles for transgene delivery. Conditionally replicative and oncolytic adenoviruses have shown great promise in the treatment of cancer (Yu et al., Curr. Opin. Mol. Ther. 2002, October; 4(5):435–43, Bell et al., Curr. Gene Ther. 2002 May 2(2): 243–54; Yoon et al. Curr. Cancer Drug Targets 2002 August; 1(2):85–107). The features which make recombinant adenoviruses potentially powerful gene delivery vectors have been extensively reviewed (Berkner, Biotechniques 6: 616–629, (1988) and Kozarsky & Wilson, Curr. Opin. Genet. Dev. 3: 499–503, (1993)). Controlled replication of adenoviral vectors, whether through gene deletion or replication restricted to particular tissues, is of particular importance for in vivo applications involving adenovirus.

Replicative adenoviruses have been engineered to achieve selective targeting and amplification for the treatment of local and disseminated cancer. Such an agent can be delivered systemically, can be targeted to tumor cells, and can amplify its cytolytic effect in a tumor-specific manner, thereby providing substantial clinical benefit. See Henderson et al., U.S. Pat. No. 5,698,443; Hallenbeck et al., WO 96/17053. In such systems, a cell-specific transcriptional regulatory element controls the expression of a gene essential for viral replication, and thus, viral replication is limited to a cell population in which the element is functional. For example, an attenuated, replication-competent adenovirus has been generated by inserting the prostate-specific antigen (PSA) promoter and enhancer (PSE-TRE) upstream of the E1A transcription unit in adenovirus serotype 5 (Ad5), which virus demonstrates selective cytotoxicity toward PSA expressing cells in vitro and in vivo (Rodriguez et al. (1997) Cancer Res. 57:2559–2563).

Helper virus-independent production of adenovirus can require a packaging cell line that complements for viral gene products. Adenovirus of interest, including oncolytic adenovirus, conditionally replicative adenovirus, and replication defective adenovirus are frequently engineered to have genetic modifications in the E1 early gene region (genetic map units 1.30 to 9.24) of the virus genome. Typical modifications include deletions within the E1 gene region and/or replacement of the E1A promoter with a tissue-specific promoter, e.g. myosin light chain, keratin, PKG, etc.

In order to produce recombinant Ad vectors for gene therapy research and trials, a packaging cell line is transfected with adenoviral E1 coding sequences. The cell line must express sufficient E1 gene products to supply in trans the E1A and E1B gene products that are required directly and indirectly for viral DNA replication and virion production.

Although E1 complementation permits the production of recombinant Ad vectors, recombination events between the transfected E1 sequences in the host cell and the Ad vector can, occur, resulting in the generation of replication competent adenovirus (RCA). This is especially problematic with large-scale production and successive propagation, such as that involved in the preparation of adenoviral particle stocks for therapeutic uses. Recombination and the development of RCA during recombinant Ad vector production not only contaminates viral stocks, but also is problematic relative to use of Adenoviral vectors for in vivo applications.

Available packaging cell lines typically contain Ad genes that have been deleted from the vector but are required for viral replication. In some cases overlapping sequences between the host cell and adenoviral vector are not completely eliminated. For example, the human embryonic kidney derived 293 cells (Graham et al. (1977) J. General Virology 36:59–74) have been widely used for propagating Adenoviral vectors. However, due to substantial overlapping sequences between the Adenoviral vector genome and the 293 cell line, recombination events occur that result in the generation of a replication competent adenoviral particles.

Improvements have been made to reduce the possibility of generating replication competent vectors due to recombination events between the packaging cell line and the vector via reduction in the sequences common to the vector and cell line (Fallaux et al. (1998) Human Gene Therapy 9:1909–1917). For example, U.S. Pat. No. 5,994,128 describes cell lines that complement for both E1A and/or E1B, while retaining the natural E1B promoter sequences. Studies performed using the PER.C6 cell line demonstrated that, despite a single region of homology between this cell line and the adenoviral vector, RCA were generated and cytopathic effects were observed in a cell based assay (Kim et al. (2001) Exp. Mol. Med. 33(3)145–9). When analyzed, the RCA were shown to contain the PGK promoter-E1 gene, derived from the plasmid that was employed to construct the PER.C6 cell line. The same problem of residual sequence overlap is true of other cell lines developed as alternatives to 293 cells (see, for example, Massie et al., U.S. Pat. No. 5,891,690; Kovesdi et al., WO 95/34671, Kedan et al., PCT/US95/15947, Schiedner et al. (2002) Human Gene Therapy, 11:2105–2116). Consequently, there remains the potential for unwanted recombination events between the cell line and the adenoviral vector.

SUMMARY OF THE INVENTION

Adenovirus packaging cell lines are provided, wherein the cells comprise E1A and E1B coding sequences, which complement deficiencies in adenoviral vectors and allow growth of an E1A/E1B deficient adenovirus. The E1A and E1B sequences are operably linked to promoters that lack polynucleotide sequences sharing substantial sequence identity with native or wild type adenovirus E1A and E1B promoters. Such packaging cell lines reliably produce stocks of adenoviral particles with minimal potential for recombination events between the packaging cell line genome and the adenoviral vector. Viral stocks produced using the packaging lines of the invention are characterized by minimal or undetectable levels of RCA with maintenance of the intended recombination genotype.

In one embodiment of the invention, the packaging cell lines comprise stably integrated E1A and E1B expression vectors, where the E1A and E1B genes are operatively linked to a non-adenovirus heterologous promoter, which may be the same or different.

In another embodiment of the invention, methods for producing adenovirus substantially free of RCA are provided, wherein the adenovirus is grown in a cell line lacking polynucleotide sequences sharing substantial sequence identity with the adenovirus E1A and E1B promoters.

DETAILED DESCRIPTION OF THE EMBODIMENTS

Figure 1:
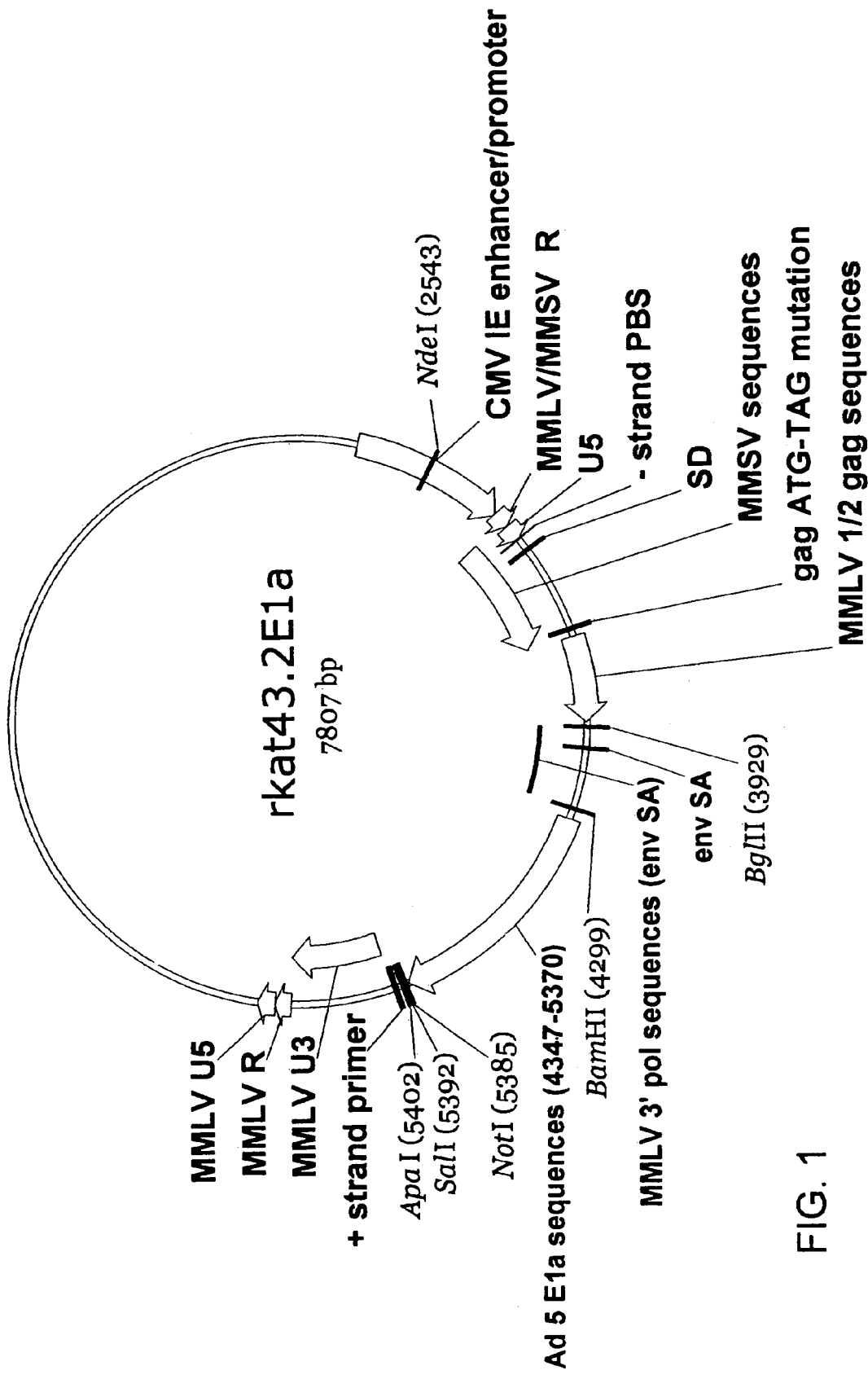
FIG. 1 illustrates an MMLV-E1A retroviral expression cassette that is free from adenoviral E1A and E1B promoter sequences.

Adenovirus packaging cell lines are provided, wherein the packaging cells provide adenovirus E1A and E1B sequences sufficient to complement and replicate an E1A/E1B deficient adenovirus, with minimal potential for generating wild type replication competent adenovirus (RCA). As used herein, RCA are replication competent adenovirus that do not require complementation by a packaging cell line for expression of E1A and/or E1B.

In packaging cell lines of interest, the adenovirus E1A and E1B coding sequences are operably linked to promoters that lack polynucleotide sequences sharing substantial sequence identity with native adenovirus E1A and E1B promoters. Such packaging cell lines reliably produce stocks of replication deficient adenoviral particles free from recombination events between the packaging cell line genome and the replication defective adenoviral vector thereby minimizing the possibility of the generation of RCA.

In one embodiment of the invention, the packaging cell lines comprise stably integrated E1A and E1B expression vectors, where the E1A and E1B genes are operatively linked to a non-adenovirus promoter and have been introduced using separate expression vectors. The promoter may be a strong constitutive promoter of non-adenovirus origin. In one embodiment, the promoter operably linked to E1A is different than the promoter linked to E1B. In another embodiment, the promoter linked to E1A is the same as the promoter linked to E1B. The E1A and E1B genes may be coordinately expressed with such a promoter.

The E1A and E1B coding regions are preferably stably integrated in the packaging cell line genome. In a preferred embodiment, the site of E1A integration is physically separated from the site of E1B integration, e.g. on separate chromosomes, separate regions of the same chromosome, and the like.

In another embodiment of the invention, methods for producing adenovirus substantially free of RCA are provided, wherein the adenovirus is grown in a cell line lacking polynucleotide sequences sharing substantial sequence identity with the adenovirus E1A and E1B promoters.

Adenoviral vectors of interest for replication in the cell lines of the invention are deficient in expression of adenovirus genes essential for replication, particularly the adenoviral E1A and E1B genes. Such vectors are unable to produce sufficient viral proteins required for productive infection in the absence of exogenously provided viral genes. Adenoviral vectors deficient in expression of E1A and E1B may be deficient due to a variety of genetic changes, e.g. a lack of coding sequences for one or both of these genes; mutations in the coding sequences that render the polypeptide inoperable; alterations in promoter or enhancer sequences, and the like.

In some embodiments of the invention, the adenovirus vector is replication competent in a targeted cell type e.g. targeted tumor cells such as prostate cancer, liver cancer, etc., but in a non-targeted cell type the adenovirus is deficient in E1A and/or E1B expression. For example, the adenovirus vector may comprise adenoviral genes essential for replication that are operably linked to a transcriptional regulatory element that is cell type specific, cell state specific, etc. Such vectors benefit from growth in a packaging cell line such as described herein, e.g. to generate large numbers of virus particles in vitro.

The various methods and formulations of the invention will be described below. Although particular methods are exemplified in the discussion below, it is understood that any of a number of alternative methods are applicable and suitable for use in practicing the invention. It will also be understood that an evaluation of the adenovirus vectors and methods of the invention may be carried out using procedures standard in the art, including the diagnostic and assessment methods described below.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

For techniques related to adenovirus, see, inter alia, Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Site-specific DNA cleavage is performed by treating with the suitable restriction enzyme (or enzymes) under conditions which are generally understood in the art, and the particulars of which are specified by the manufacturer of these commercially available restriction enzymes. (See, e.g. New England Biolabs, Product Catalog.) In general, about 1

μg of plasmid or DNA sequences is cleaved by one unit of enzyme in about 20 μl of buffer solution. Typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods of Enzymology 65:499–560 (1980) (see also, Sambrook and Russell, supra).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° C. in 50 mM Tris (pH 7.6) 50 mM NaCl, 6 mM $MgCl_2$, 6 mM DTT and 5–10 μM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with SI nuclease or Bal-31 results in hydrolysis of any single-stranded portion.

Ligations are performed in 15–50 μl volumes under the following standard conditions and temperatures: 20 mM Tris-Cl pH 7.5, 10 mM $MgCl_2$, 10 mM DTT, 33 mg/ml BSA, 10 mM–50 mM NaCl, and either 40 μM ATP, 0.01–0.02 (Weiss) units T4 DNA ligase at 0° C. (for "sticky end" ligation) or 1 mM: ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 mM total end concentration). Intermolecular blunt end ligations (usually employing a 10–30 fold molar excess of linkers) are performed at 1 μM total ends concentration.

Unless otherwise indicated, all terms used herein have the same meaning as they would to one skilled in the art and the practice of the present invention will employ, conventional techniques of microbiology and recombinant DNA technology, which are within the knowledge of those of skill of the art.

A "packaging cell line" is a eukaryotic cell population that is permissive for replication of human adenovirus deficient in E1A/E1B. The packaging cell line is produced by genetically modifying a cell line permissive for adenovirus replication, to comprise adenovirus E1A and E1B coding sequences. The adenovirus E1A and E1B coding sequences are operably linked to promoters that lack polynucleotide sequences sharing substantial sequence identity with adenovirus E1A and E1B promoters.

As used herein, substantial sequence identity refers to the level of sequence similarity that is sufficient for homologous recombination within the host cell. Candidate sequences can be empirically tested for recombination by, for example, testing two sequences for recombination during replication in the cell of interest. Typically, a sequence will lack substantial sequence identity if there is not more than about 20 nucleotides of contiguous, identical polynucleotide sequence, more usually not more than about 15 nucleotides of contiguous, identical polynucleotide sequence, and preferably not more than about 12 nucleotides of contiguous, identical polynucleotide sequence. The reference sequence will usually be the adenovirus from which the vector is derived, e.g. human adenovirus 5; human adenovirus 2; etc. The lack of substantial sequence identity between the promoters driving expression of E1A and E1B in the packaging cell lines of the invention, and endogenous adenovirus E1A and E1B promoters, will minimize the possibility of recombination and resulting replication competent adenovirus (RCA) production.

The term "adenovirus permissive" means that the adenovirus or adenoviral vector is able to complete the entire intracellular virus life cycle within the cellular environment. The cells may be derived from primary cell cultures, from established cell lines, and the like. Mammalian cells are preferred, including primate cells, e.g. human cells, monkey cells, etc. Although various primate cells are preferred and such human embryonic kidney cells are more preferred, any type of cell that is capable of supporting replication of the virus is acceptable in the practice of the invention.

Some preferred cell lines include human tumor cell lines. In a preferred embodiment the packaging cell line is derived from PC-3 cells. (ATCC number CRL-1435). PC-3 cells were initiated from a metastatic prostate cell adenocarcinoma. PC-3 cells are particularly advantageous for the large-scale production of clinical grade Ad vectors as they can be adapted for passage in serum free media. In another embodiment, the packaging cell line is derived from the human embryonic kidney cell line, 293. Other cell types might include, but are not limited to, Vero cells, CHO cells or any eukaryotic cells for which tissue culture techniques are established, as long as the cells are adenovirus permissive. In a further embodiment, the cells are derived from primary cell cultures, e.g., human primary prostate cells. Eukaryotic dipolid and aneuploid cell lines are included within the scope of the invention.

A candidate cell line may be tested for its ability to support adenovirus replication by methods known in the art, e.g. by contacting a layer of uninfected cells, or cells infected with one or more helper viruses, with virus particles, followed by incubation of the cells. The formation of viral plaques, or cell free areas in the cell layer, is the result of cell lysis caused by the expression of certain viral products. Cell lysis is indicative of viral replication.

In one embodiment, the packaging cell line is both permissive for adenovirus replication, and adenovirus infection. The primary receptor of adenovirus serotypes 2 and 5 has been identified and named CAR (Coxsackievirus and Adenovirus Receptor; GenBank Accession no. HSU90716) by Bergelson et al. (1997) Science 275:1320, and shown to be a receptor for all adenovirus subgroups except subgroup B by Roelvink et al. (1998). CAR is an uncharacterized cell surface protein and different cells have different levels of CAR expression. Permissive cells generally express a level of CAR sufficient for infection.

"Replication" and "propagation" are used interchangeably and refer to the ability of an adenovirus vector to reproduce or proliferate. These terms are well understood in the art. For purposes of this invention, replication involves production of adenovirus proteins and is generally directed to reproduction of adenovirus. Replication can be measured using assays standard in the art and described herein, such as a virus yield assay, burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

The packaging cell line comprises genetic sequences encoding human adenovirus E1A and E1B proteins. The sequence of many such proteins, e.g. from human adenovirus type 11; human adenovirus 41; human adenovirus 12; human adenovirus 5; human adenovirus 41; human adenovirus 40; human adenovirus 4; human adenovirus 7; and human adenovirus 2 are known and publicly available. See, for example, the E1A polypeptide sequences, Genbank accession numbers AAN62486 (Ad 11), Q2AD5 (Ad 5); Q2AD2 (Ad2); and the E1B polypeptide sequences, Genbank Accession numbers Q1AD25 (Ad5); and Q1AD22 (Ad2). The origin of the E1A and E1B coding sequences are most preferably from human Ad5. Other human and non-human adenoviral serotypes may also be used, including Ad2. The E1A and E1B sequences used in the present invention do not include the promoter sequences of either E1A or E1B. Usually the packaging line will not include adenovirus genetic sequences other than the E1A and E1B coding sequence.

A packaging cell line according to the present invention is useful for the large-scale production of clinical grade Ad vectors derived from any known adenovirus serotype, as well as chimeric adenoviruses comprised of sequences derived from more than one serotype.

As used herein, the term E1A refers to all gene products of the adenovirus E1A region, including expression products of the two major RNAs: 13S and 12S. These are translated into polypeptides of 289 (SEQ ID NO:2) and 243 (SEQ ID NO:3) amino acids, respectively. These two proteins differ by 46 amino acids, which are spliced from the 12S mRNA, as described in Chow et al. (1980) Cold Spring Harb Symp Quant Biol. 44 Pt 1:401-14; and Chow et al. (1979) J Mol. Biol. 134(2):265–303, herein specifically incorporated by reference. For the purposes of the invention, the packaging cell line may express the 289 polypeptide, the 243 polypeptide, or both the 289 and the 243 polypeptide.

As used herein, the term E1B refers to all gene products of the adenovirus E1B region, including the 3 major polypeptides, of 19 kd (SEQ ID NO:5) and 55 kd (SEQ ID NO:6). The E1B 19 kd and 55 kd proteins are important in cell transformation. For the purposes of the invention, the packaging cell line may express the 19 Kd polypeptide, the 55 Kd polypeptide, or both the 19 and the 55 Kd polypeptide.

Exemplary E1A and E1B coding sequences comprise two exon regions of E1A, which correspond to nucleotides 560–1545 of GenBank Accession No. M73260 or X02996 (presented herein as SEQ ID NO:1) and two E1B coding sequences that corresponds to nucleotides 1682–3825 of GenBank Accession No. M73260 or X02996 (presented herein as SEQ ID NO:4). It will be understood by one of skill in the art that the adenovirus sequences provided herein are merely examples of suitable sequences, as many adenovirus genomes have been characterized and are available for use.

| SEQ ID NO | Name | Length | Type |
|---|---|---|---|
| 1 | E1A genomic sequence | 986 | DNA |
| 2 | E1A 289 | 289 | Protein |
| 3 | E1A 243 | 243 | Protein |
| 4 | E1B genomic sequence | 2144 | DNA |

-continued

| SEQ ID NO | Name | Length | Type |
|---|---|---|---|
| 5 | E1B 19K | 176 | Protein |
| 6 | E1B 55K | 496 | Protein |
| 7 | E1A 289R cDNA | 873 | DNA |
| 8 | E1B 55K cDNA | 1491 | DNA |

The E1A and E1B sequences are operably linked to a non-Ad promoter. The promoter may be heterologous, where the term "heterologous" promoter is used herein to mean a promoter sequence that is not native to the packaging cell. Alternatively a homologous promoter is used, which is native to the packaging cell. For replication of adenovirus vectors comprising coding sequences for E1A and/or E1B, the promoter for E1A and/or E1B in the packaging cell line is preferably other than the promoter operably linked to E1A and/or E1B in the adenovirus vector.

Nucleic acids are "operably linked" when placed into a functional relationship with another nucleic acid sequence. For example, a promoter or enhancer is operably linked to a coding sequence if it affects the transcription of the sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adapters or linkers are used in accordance with conventional practice.

The promoter sequences used to express E1A and E1B may be identical or non-identical. Where the promoter sequences are identical, the E1A and E1B coding sequences may be coordinately expressed, e.g. where both coding sequences are operatively linked to a single promoter and an IRES is present between the two coding sequences. As used herein, an "internal ribosome entry site" or "IRES" refers to an element that promotes direct internal ribosome entry to the initiation codon, such as ATG, of a cistron (a protein encoding region), thereby leading to the cap-independent translation of the gene (Jackson et al. (1990) Trends Biochem Sci 15(12):477–83) and Jackson et al. (1995) RNA 1(10): 985–1000). The present invention encompasses the use of any IRES element that is able to direct internal ribosome entry to the initiation codon of a cistron. "Under translational control of an IRES" as used herein means that translation is associated with the IRES and proceeds in a cap-independent manner. Examples of "IRES" known in the art include, but are not limited to IRES obtainable from picornavirus (Jackson et al., 1990, Trends Biochem Sci 15(12):477–483); and IRES obtainable from viral or cellular mRNA sources, such as for example, immunoglobulin heavy-chain binding protein (BiP), the vascular endothelial growth factor (VEGF) (Huez et al. (1998) Mol. Cell. Biol. 18(11):6178–6190), the fibroblast growth factor 2, and insulin-like growth factor, the translational initiation factor eIF4G, yeast transcription factors TFIID and HAP4. See also, Li, Y et al., Cancer Research, 2001; 17: 6428–6436; Zhang, J et al., Cancer Research, 2002; 13: 3743–3750) and WO01/73093 (expressly incorporated by reference herein) which describes cell-specific adenovirus vectors comprising an internal ribosome entry site. IRES have also been reported in different viruses such as cardiovirus, rhinovirus, aphthovirus, HCV, Friend murine leukemia virus (FrMLV) and Moloney murine leukemia virus (MoMLV).

As used herein, the term "IRES" encompasses functional variations of IRES sequences as long as the variation is able to promote direct internal ribosome entry to the initiation codon of a cistron. In preferred embodiments, the IRES is mammalian. In other embodiments, the IRES is viral or protozoan. In one illustrative embodiment disclosed herein, the IRES is obtainable from encephelomycarditis virus (ECMV) (commercially available from Novogen, Duke et al. (1992) *J. Virol* 66(3):1602–1609). In another illustrative embodiment disclosed herein, the IRES is from VEGF.

The linking of proteins in the form of polyproteins is a strategy adopted in the replication of many viruses including picornaviridae. Upon translation, virus-encoded peptides mediate rapid intramolecular (cis) cleavage of a polyprotein to yield discrete mature protein products. Accordingly, the invention described herein may comprise a 2A or 2A-like sequence which provides the opportunity to express E1A and E1B under transcriptional control of a single promoter such that the proteins are cleaved apart co-translationally with high efficiency. Constructs including the essential amino acid residues for expression of the cleavage activity by the FMDV 2A region have been designed (Ryan et al. (1991) *J. Gen. Virol.* 72:2727–2732; Furler et al. (2001) *Gene Therapy* 8: 864–873). 2A domains have also been characterized from aphthoviridea and cardioviridae of the picornavirus family (Donnelly et al. (1997) *J. Gen. Virol.* 78:13–21.

In one embodiment of the present invention, one or both promoters are regulatable promoters, e.g., promoters inducible with an agent, such as metals or hormones (Brinster et al. *Nature* (1982), 296, 39–42), or hormones (Lee et al. *P.N.A.S.* USA (1988), 85, 1204–1208; (1981), 294, 228–232; Klock et al. *Nature* (1987), 329, 734–736; Israel and Kaufman, *Nucleic Acids Res.* (1989), 17, 2589–2604).

Alternatively, in yet another embodiment, the promoter is a constitutive promoter. Promoters can be obtained from the genomes of viruses such as polyoma virus, fowlpox virus, bovine papilloma virus, avian sarcoma virus, cytomegalovirus, a retrovirus, hepatitis-B virus and Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

In one exemplary embodiment the LTR of MMLV is operatively linked to the E1A gene in a first retroviral expression vector and in a second retroviral expression vector, the LTR of MMLV is also used to direct the expression of the E1B gene. In another exemplary embodiment the CAG promoter is operatively linked to exon 1 and exon 2 of the E1A gene (SEQ ID NO:1) in a first expression vector and in a second expression vector, the EF1-alpha promoter is used to direct the expression of a 19 k and a 55 k E1B coding sequence (SEQ ID NO:4).

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, etc. The enhancer may be spliced into the expression vector at a position 5' or 3' to the coding sequence, but is preferably located at a site 5' from the promoter.

A vector comprising E1A or E1B is introduced into a permissive host cell. Many such vectors are available, including plasmid vectors, viral vectors, etc. The vector components may include, but are not limited to, one or more of the following: an origin of replication, one or more marker genes, an enhancer element, a promoter, and a transcription termination sequence.

Preferred expression vectors for the introduction of E1A/E1B coding sequences are those capable of stable integration in a host cell that are maintained at high frequency in daughter cells. In one preferred embodiment the expression vectors are of viral origin. In another preferred embodiment, the expression vector is a plasmid derived from a retrovirus. In another embodiment the expression vector is a plasmid derived from a lentivirus. Hybrid vectors may also be used, which contain sequences from a retrovirus and a second non-Ad virus. In a further preferred embodiment, the expression vector is a retroviral vector derived from Moloney Murine Leukemia Virus (MMLV), which has a cloning capacity of at least 7.5 kilobases. Non-viral expression vectors may alternatively be used so long as they contain genetic elements that facilitate integration into the host cell genome. Expression vectors of the present invention may additionally contain non-coding and coding sequences, including those imparting selectable traits to the cell line.

The resulting E1A and E1B expression vectors may be introduced into the cell line sequentially or simultaneously using standard transfection methods (Sambrook, supra), or in the most preferred embodiment, packaged into infectious viral particles and introduced into the cell line via transduction. As would be readily understood, the term "introduced" embraces any methodology employed to deliver DNA sequences into a cell, including transduction and transfection methods as appropriate to the expression vector (e.g., infectious particles versus DNA plasmids). Using separate expression vectors for E1A and E1B, respectively, introduced sequentially or simultaneously, further reduces potential recombination events between the packaging cell genome and an Ad vector, as each integrates into the packaging cell genome in a different location. The invention provides the advantage of spatial separation of the expression vectors within the genome, providing for the further decrease in recombination events that could generate RCA or a loss of tissue specific replication.

Host cells are transfected with the above-described expression vectors for E1A/E1B polypeptide production, and cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

An "adenovirus vector" or "adenoviral vector" (used interchangeably) of the invention is a polynucleotide construct that provides for an E1A/E1B deficient adenovirus; which in some embodiments will exhibit preferential replication in target cells and contain a tissue-specific transcriptional regulatory sequence linked to an adenoviral gene essential for replication (i.e., E1A and/or E1B). Exemplary adenoviral vectors of the invention include, but are not limited to, DNA, DNA encapsulated in an adenovirus coat, adenoviral DNA packaged in another viral or viral-like form (such as herpes simplex, and AAV), adenoviral DNA encapsulated in liposomes, adenoviral DNA complexed with polylysine, adenoviral DNA complexed with synthetic polycationic molecules, conjugated with transferrin, or complexed with compounds such as PEG to immunologically "mask" the antigenicity and/or increase half-life, or conjugated to a nonviral protein.

Adenovirus sequences useful in this invention include the DNA sequences of a number of adenovirus types, many of which are available from Genbank. The adenovirus sequences may be obtained from any known adenovirus serotype, such as serotypes 2, 3, 4, 5, 6, 7, 12 and 40. Similarly adenoviruses known to infect other animals may also be employed in the vector constructs of this invention. The selection of the adenovirus type is not anticipated to limit the following invention. A variety of adenovirus strains are available from the American Type Culture Collection, Manassas, Va., or available by request from a variety of commercial and institutional sources. Recombinant adenoviruses deficient in E1A/E1B may include deletion or other genetic modification in the E1 region. Recombinant adenoviruses useful in this invention may optionally bear other genetic changes, e.g. inclusion of a transgene, and the like.

After replication in the packaging cell lines of the invention, the population of adenovirus vector of interest is substantially free of RCA. Substantially free of RCA means that the amount of RCA is sufficiently low that no toxicity results from in vivo administration of adenoviral vectors produced using the cell lines of the invention. Preferably, an adenovirus vector preparation that is substantially free of RCA contains from about zero to about 1 in about $10^4$ RCA particles per patient dose. However, by way of example, a patient dose of $10^{13}$ total viral particles may contain from zero to 10, $10^2$, $10^3$, $10^4$, $10^5$, $10^6$, $10^7$ or $5\times 10^7$ recombinant viral particles and be considered to be substantially free of RCA, so long as no toxicity results following in vivo administration.

An adenovirus vector encapsulated in an adenovirus coat, or in another viral or viral-like form, will generally be the form that is purified, although the DNA and other forms may find use, for example, in the initial infection steps. The term "adenovirus", or "adenovirus particle" may be used interchangeably to refer to such an encapsulated vector.

The adenovirus population may be formulated for use, e.g. in clinical applications. The eluant is optionally concentrated and diafiltered by conventional methods, e.g. with a hollow fiber concentrator. In a final preparation for use, the virus sample may be sterile filtered. A variety of filters suitable for this purpose are known in the art, e.g. nitrocellulose membrane filters; cellulose acetate membrane filters; PVDF (modified polyvinylidene fluoride) membrane filters; and the like. Preferred are PVDF membrane filters (for example. Millipore Millipak filters).

The sterile filtered virus suspension is formulated for use in vitro or in vivo. Aqueous compositions comprise an effective amount of the virus, suspended in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Formulations include injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical composition are adjusted according to well-known parameters.

Formulations may be optimized for the desired storage conditions. In one embodiment of the invention, particularly with virus formulated for clinical use, the samples are stored in liquid form, preferably at cool temperatures, usually less than about 10° C., more usually less than about 5° C. For such conditions, a preferred medium for storage comprises 5% sucrose, 1% glycine, 1 mM $MgCl_2$, 10 mM Tris, and small amounts of a surfactant. One surfactant of interest is a non-ionic detergent, e.g. Tween 80, Tween 20, etc., at a concentration of from about 0.01% to about 0.1%, preferably about 0.05%. Other surfactants of interest include poloxamer block polymers of polyethylene glycol polypropylene glycol such as Lutrol F-68, Lutrol F-127, etc., e.g. at a concentration of from about 5% to about 10%, preferably about 8%.

For samples that are stored frozen, for example at −20° C. or −80° C., suitable buffers are as described above, however the inclusion of surfactants is generally less important to stability, and may be omitted. Glycerol at a concentration of from about 2% to about 10% may be included.

The viral particles of the present invention may include classic pharmaceutical preparations for use in therapeutic regimens, including their administration to humans. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal, or intravenous injection. Such compositions would normally be administered as pharmaceutically acceptable compositions that include physiologically acceptable carriers, buffers or other excipients. For application against tumors, direct intratumoral injection, injection to a resected tumor bed, regional (i.e., lymphatic) or general administration is contemplated. It also may be desired to perform continuous perfusion over hours or days via a catheter to a disease site, e.g., a tumor or tumor site.

An effective amount of the adenovirus vector may be administered to a patient as a composition in a pharmaceutically acceptable excipient (and may or may not be in the same compositions), including, but not limited to, saline solutions, suitable buffers, preservatives, stabilizers, and may be administered in conjunction with suitable agents such as antiemetics. An effective amount is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state. Some individuals are refractory to these treatments, and it is understood that the methods encompass administration to these individuals. The amount to be given will be determined by the condition of the individual, the extent of disease, the route of administration, how many doses will be administered, and the desired objective.

An effective amount of the therapeutic agent is determined based on the intended goal, for example (i) inhibition of tumor cell proliferation, (ii) elimination or killing of tumor cells, (iii) vaccination, and the like. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the result desired.

Assessment of the efficacy of a particular treatment regimen may be determined by any of the techniques known in the art, including diagnostic methods such as imaging techniques, analysis of serum tumor markers, biopsy, and/or an evaluation of the presence, absence or amelioration of tumor associated symptoms. It will be understood that a given treatment regime may be modified, as appropriate, to maximize efficacy.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

Construction of E1A/E1B Packaging Cell Lines

Construction of MMLV Expression Vectors. Moloney Murine Leukemia Virus (MMLV)-derived plasmids were utilized for constructing an E1A retroviral expression vector and an E1B retroviral expression vector. Specifically, the pRT43.2F3 plasmid was utilized. The construction of pRT43.2F3 is summarized below and is completely described in U.S. Pat. No. 5,686,279, which is incorporated herein by reference in its entirety.

pRT43.2F3. This retroviral vector contains modified 5' LTRs that direct efficient transcription in the cell type where retrovirus is to be produced. The retroviral vectors of the invention are modeled after pZen (Johnson et al., *EMBO Journal* 8(2):441–448 (1989)), a neo-version of pZIPneoSVX (Cepko et al., *Cell* 37:1053–1062(1985)), in which the gene product to be expressed is cloned downstream of the splice acceptor in the position normally occupied by the neo cassette (Cepko et al., supra). In addition, viral gag sequences up to the Nar I site of MMLV (nucleotide 1038) were added for improved packaging (Armentano et al., *J. Virol.* 61:11647–1650 (1987)) and the Xho I to Cla I fragment of pZIPneoSVX was deleted (Cepko et al., supra). The Eco RI to Apa I polylinker from pIK1.1 was inserted downstream of the splice acceptor to enable transfer of inserts from pIK plasmids into retroviral constructs. The resulting plasmid is designated pRTD1.2 and contains both 5' and 3' MMLV LTRs. The 5' LTR U3 region of pZIPneoSVX was replaced with the MMSV U3, derived from the HindIII/Sac I fragment of pIKMMSV, to generate pRTD4.2.

In pRTD2.2, the U3 region of the 5' LTR of pZIPneoSVX was replaced with the Hind III/Sac I fragment from pIK1.1 encoding the CMV immediate early enhancer/promoter, which was fused to the MMLV R region by an oligonucleotide that encodes nucleotides 19 (Sac I) to +1 of the HCMV promoter linked to nucleotides +1 to +32(KpnI) of MMLV (Schinnick et al., *Nature* 293:543–548 (1980)).

pRTD2.2SVG was constructed by replacement of the (750 bp) Sac I to Bst EII fragment of pRTD2.2 with the (736 bp) Sac I to Bst EII fragment of LXSN (Miller and Rosman, *BioTechniques* 7:980–990 (1989)). pRTD2.2SSA was constructed by replacement of the (1441 bp) Sac I to Eco RI fragment of pRTD2.2 with the (1053 bp) Sac I to Eco RI fragment of LXSN (Miller and Rosman, supra). pRTD2.2SVGE- was constructed by synthesis of an oligonucleotide encoding nucleotides 2878–2955 of pLXSN (GenBank Accession Bank, M28248) which had been appended by addition of an Apa I site on it's 5' end. This was used to replace the Apa I to Nhe I fragment of pRTD2.2SVG, which contains the DNA sequence 3' of the of the polylinker and 5' of the Nhe I site in the 3' LTR. These retroviral vector constructs of the invention have a pBR322 backbone and include pRTD2.2, pRTD4.2, pRTD2.2SVG, pRTD2.2SVGE- and pRTD2.2SSA.

In order to permit plasmid replication in cells which express the SV40 T antigen, the sequences between the 5' and 3' LTRs of pRTD2.2 were cloned between the SacI and Eco RI sites of pIK1.1, described above, which contains the SV40 origin of replication to form vector pIKT2.2. pIKT2.2SVG was constructed by insertion of the fragment defined at its 5' end by the Sac I site in the HCMV promoter of pRTD2.2SVG and defined at its 3' end by an Eco RI site located 750 bp downstream of the 3' LTR of pRTD2.2SVG, between the SacI and Eco RI sites of pIK1.1. pIKT2.2SVGE-F3 was constructed by replacing the 182 base pair ApaI to NheI fragment of pIKT2.2SVGF3 with the 80 base pair ApaI to NheI fragment from pRTD2.2SVGE-F3 as described above.

pRT43.2F3 was derived from pIKT2.2SVGE-F3 by replacing the Eco RI to ApaI polylinker located approximately 750 base pairs downstream from the 3' LTR with a synthetic oligonucleotide containing an AscI recognition site. In addition, the Nde I site at the 3' end of the viral gag sequences has been converted to an XhoI site by oligonucleotide insertion. pRT43.3PGKF3 was derived from pRT43.2F3 first by removal of the 3' LTR in pRT43.2F3 and insertion of a 0.3° LTR in which the sequences from PvuII to XbaI were deleted (MMLV, GenBank session #J02255 nucleotide numbers 7938–8115). In addition the MMLV splice acceptor region has been replaced with the human phosphoglycerate kinase gene promoter (GenBank session #M11958 nucleotides 2–516), which was cloned into a polylinker with a XhoI site at its 5' end and an Eco RI at its 3' end.

E1A Expression Vector—rkat 43.2E1A. rkat 43.2E1a (FIG. 1) is a retroviral vector that expresses the Ad5 E1A open reading frame under the control of the retroviral LTR. Thus, neither an adenoviral nor mammalian host cell derived promoter is utilized for directing expression of Ad E1A. rkat 43.2E1A was generated by replacing the CD4/ξ coding sequences of pRT43.2F3 (U.S. Pat. No. 5,686,279 and Roberts et al., *J. Immunology* (1998) 161:375–384) with the DNA sequences coding for Ad5 E1A open reading frames (Ad5 nucleotides 548–1575, Genbank Accession X02992: SEQ ID NO:1).

Figure 2:
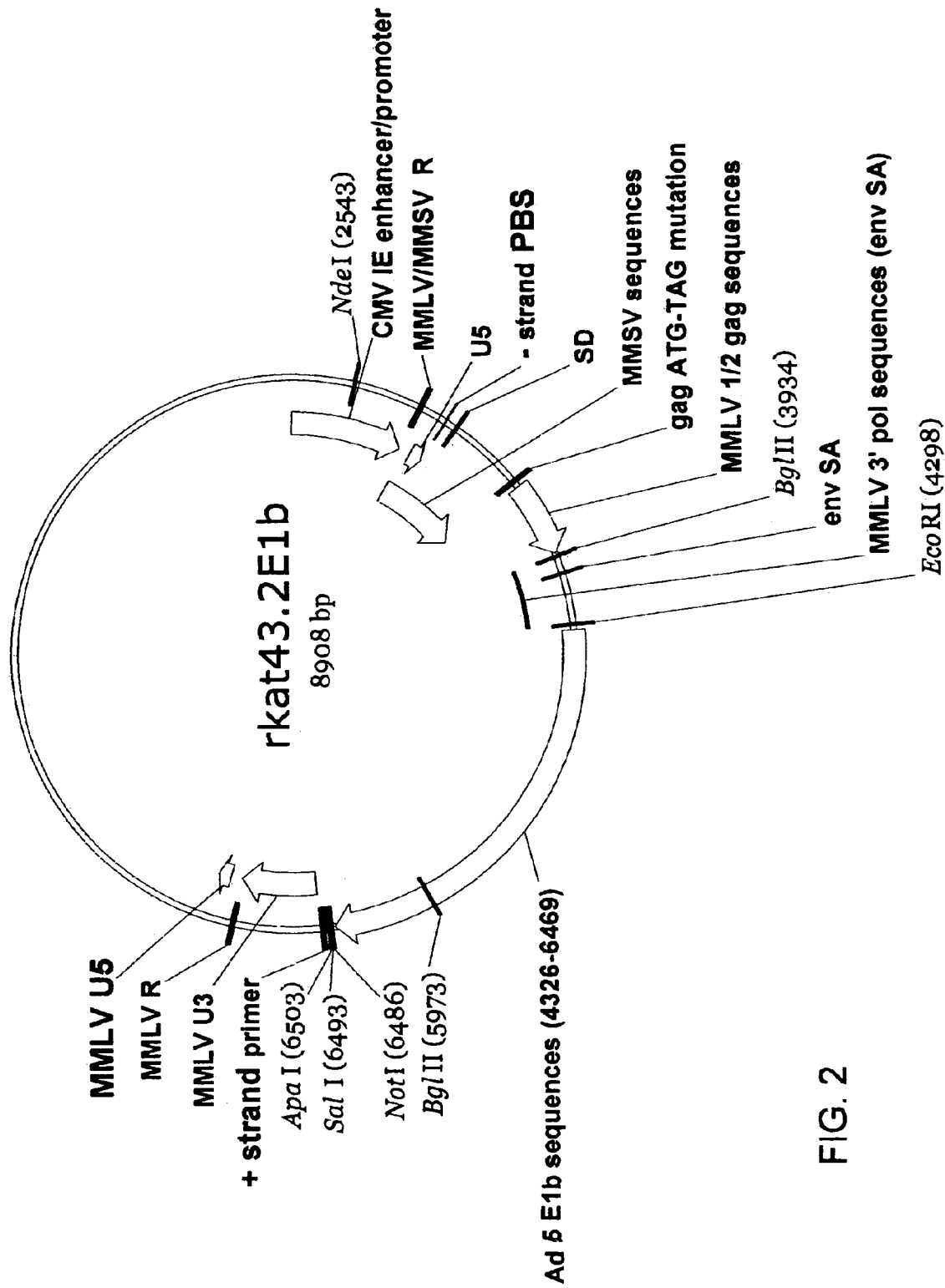
FIG. 2 illustrates an MMLV-E1B retroviral expression cassette that is free from adenoviral E1A and E1B promoter sequences.
Figure 3:
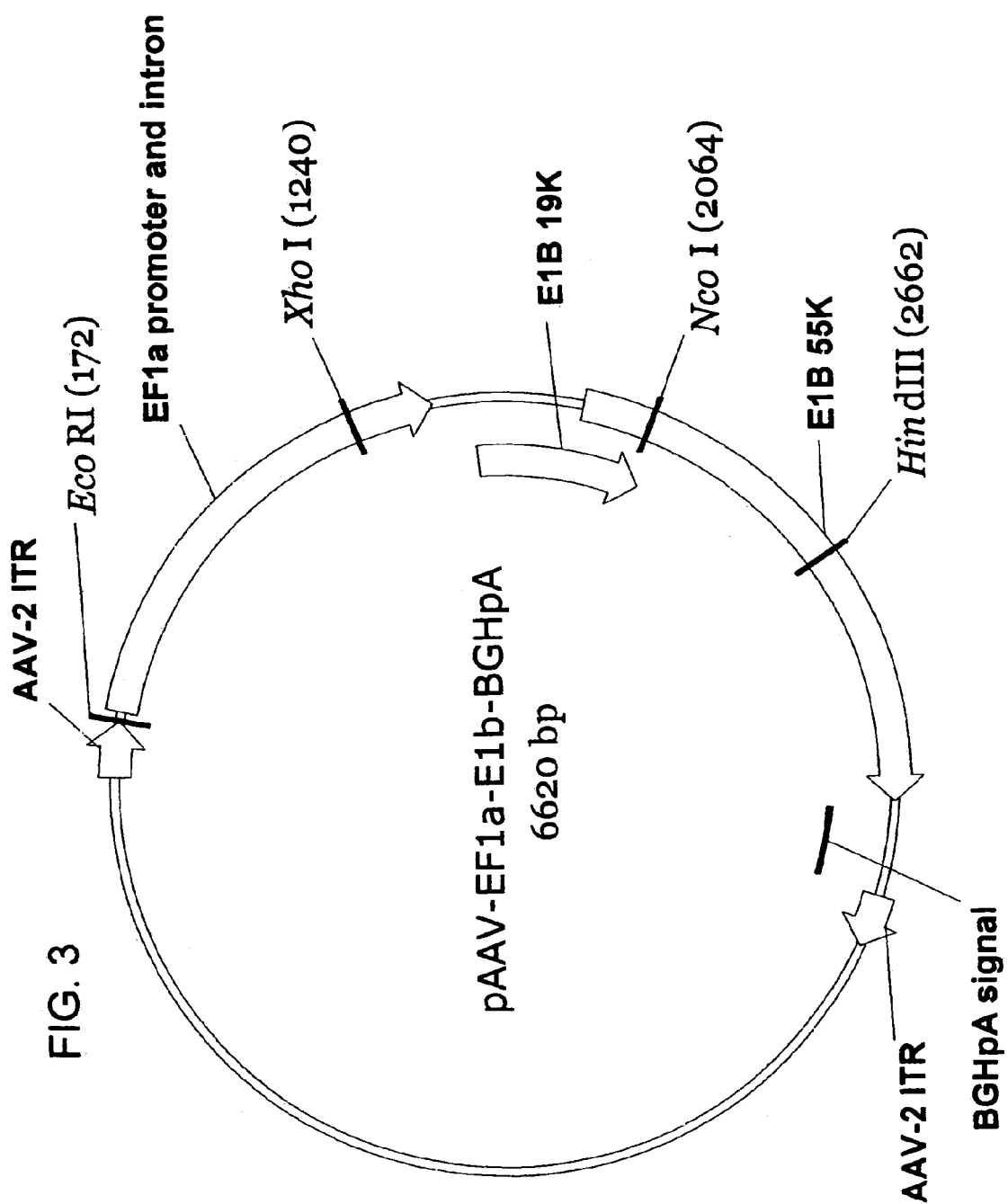
FIG. 3 illustrates an AAV-E1A expression cassette that is free from adenoviral E1A and E1B promoter sequences and includes in the 5' to 3' directions, a 5' ITR; a cytomegalovirus enhancer/chicken beta-actin/Rabbit β-globin promoter (CAG promoter; Niwa et al. (1991) *Gene* 108(2):193–9); exon 1 and exon 2 of E1A (SEQ ID NO:1); a woodchuck post-transcriptional regulatory element (WPRE); a bovine growth hormone poly A (BGHpA) sequence and a 3' ITR.
Figure 4:
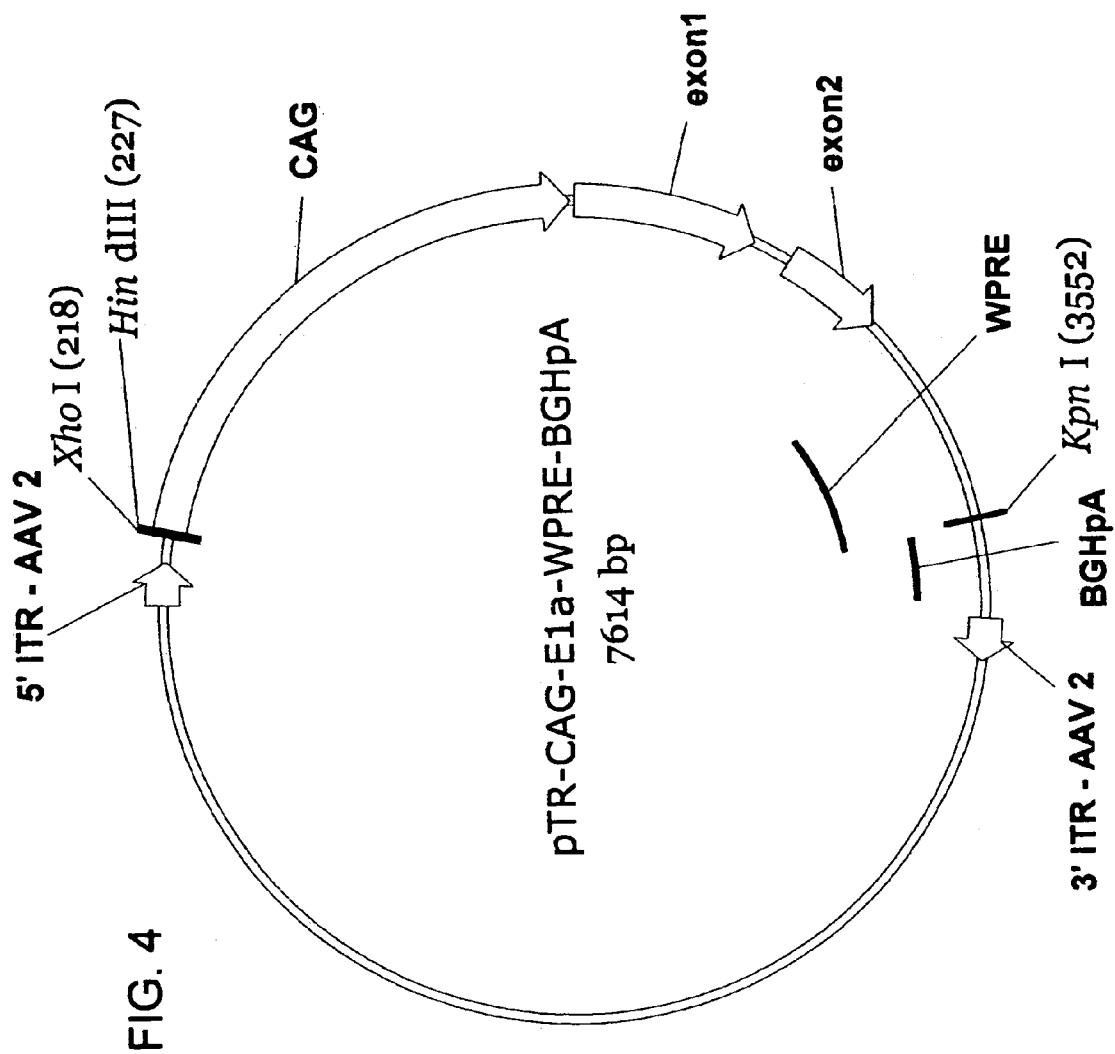
FIG. 4 illustrates an AAV-E1B expression cassette that is free from adenoviral E1A and E1B promoter sequences and includes in the 5' to 3' directions, a 5' ITR; an elongation factor 1-alpha promoter (EF1-alpha) promoter (Kim et al. (1990) *Gene* 91(2):217–23 and Guo et al. (1996) *Gene Ther.* 3(9):802–10) and enhancer; a 19K E1B coding sequence and a 55K E1B coding sequence (SEQ ID NO:4); a bovine growth hormone poly A (BGHpA) sequence and a 3' ITR.

E1B Expression Vector—rkat 43.2E1B. rkat 43.2E1B (FIG. 2) was similarly generated from pRT43.2F3. This vector expresses the Ad5 E1B open reading frames (nucleotides 1682–3825 of Ad5, Genbank Accession X02996: SEQ ID NO:4) under the control of the retroviral LTR and does not include an adenoviral or mammalian host cell derived promoter. rkat 43.2E1A was generated by replacing the CD4/ξ coding sequences of pRT43.2F3 (U.S. Pat. No. 5,686,279 and Roberts et al., supra) with the cDNA sequences coding for Ad5 E1B mRNA.

Transient Retrovirus Production. Infectious particles comprising the E1A and E1B expression vectors were produced using standard methodology. Transient viral supernatants were prepared by co-transfecting rkat 43.2E1A- or rkat 43.2E1B plasmids with MCVecog/p and 6.1CMVamphoenv. The resulting viral supernatants MMLV-E1A (designated C5.03–0.04) and MMLV-E1B (designated C5.05–0.06) were then utilized for cell transduction.

A549 Cell. Transduction. Naive A549 cells (ATCC No. CCL-185) were cultured in complete medium including DMEM/High, 10% fetal bovine serum, 1% glutamine and 1% Pen-Strep. Adenoviral E1A and E1B coding sequences were stably introduced into A549 cells by co-infecting the cells with MMLV-E1A and MMLV-E1B viruses by spinoculation. $1.5 \times 10^5$ cells were resuspended in 1 ml of E1A/E1B viral supernatants and 8 μl/ml of polybrene. The cell and virus mixture was then centrifuged at 3400 rpm at 34° C. for 4 hours. To ensure optimal E1A/E1B ratios, three different E1A/E1B viral ratios (25% E1A/75% E1B, 50% E1A/50% E1B, 75% E1A/25% E1B) were used in spinoculation. MMLV-green fluorescent protein (GFP) virus was included as a control for monitoring viral transduction efficiency. After spinoculation, the three populations were resuspended with complete medium, transferred into 6-well plates and incubated in 5% incubator at 37° C. for 8 days.

Dilutional Cloning of E1A/E1B Transduced Cells. The three populations were dilution cloned on 10-cm dishes. After 18 days in culture, there were clear differences between the three populations. Clones from all three populations were picked into 96-well plates, and duplicate plates were made. These were grown for 5 days to allow cell expansion.

Functional Screening for E1 Complementation. An E1-deficient recombinant adenovirus carrying a GFP transgene was utilized to test each of the E1A/E1B transduced clones for the ability to support adenoviral replication. One set of 96-well plates was infected with the E1-deficient Ad-GFP virus at M.O.I. of 10 at 100 μl/well for 48 hours. The cells were subject to 3× freeze/thaw cycles to release viral particles. These lysates were used to infect HuH7 cells. Three days after infection, HuH7 cells were harvested and analyzed by FACS to evaluate for GFP expression. The E1A/E1B transduced packaging cells whose supernatants gave high GFP expression in HuH7 cells were further characterized.

Interestingly the 50%-E1A 50%-E1B cell population had the fewest number of surviving "healthy" clones, as determined by morphology, prior to infection with $E1^{31}$Ad-GFP, but produced a higher proportion of clones complementing E1 deficient viruses. The clones arising from the 75% E1A/25% E1B transduction ratio had the best overall growth characteristics, but did not yield the same observed complementation of the E1 deficient virus of the 50%-E1A 50%-E1B clones.

Characterization of Genomic Integration in Packaging Cell Lines. The separate expression vectors utilized for co-transfecting the E1A and E1B genes integrate into the host cell genome at different locations, which serves to further reduce any possibility of recombination between a replication defective Ad vector and the packaging cell lines of the present invention. Southern analysis of each E1A/E1B packaging cell line is performed using E1A- and E1B sequence specific probes to confirm the presence of at least one copy of each expression cassette per cell. In addition, identifying the site of integration is performed using fluorescence in situ hybridization (FISH), with or without simultaneous immunostaining (Adenovirus Methods and Protocols, Ed. W. S. M. Wold, Methods in Molecular Medicine, Humana Press, 1998).

Protein Analysis of E1A/E1B Transduced A549 Cells. Western blot analysis is performed using methods widely known in the art (e.g., Anton and Graham, J. Virology, 69, 4600–4606, 1995, Sambrook and Russell, supra). Briefly, E1A/E1B packaging cells are grown to subconfluence. Cultures are washed, scraped and lysates cleared by centrifugation. Protein concentrations measured using BioRad assay kit. Twenty micrograms of total cellular protein is loaded on 12.5% SDS-polyacrylamide gel and subject to electrophoresis. Mock transduced A549 cells (transduced with MMLV vector without E1A or E1B coding sequences), and 293 or PER.C6 cell lysates are used as negative and positive controls, respectively. Alternatively, purified E1A and E1B proteins of known concentration may be used as the positive controls. The separated proteins are transferred to a nitrocellulose membrane and blocked according to standard methods (e.g., 1% BSA in TBS with 0.05% Tween-20 for 1 hour). Any commercially available antibody specific for E1A proteins (289R and 243R) and E1B proteins (21 kB/19 kB and 55 kB) may be utilized as a primary antibody. M73, a mouse monoclonal antibody (Harlow et al., 1985; available from Santa Cruz Biotechnology Inc.), is used to for detecting E1A proteins. Alternatively, M58 may be used (Pharmingen). For Ad5-E1B-21K and -55K proteins, antibodies DP07L and DP08 are used (Calbiochem). If the packaging cell lines utilized Ad2-E1B sequences, then the corresponding anti-19K antibodies, DP16 or DP17 are used. Secondary antibodies labeled with horseradish peroxidase or enzyme (e.g., alkaline phosphatase) are used in accordance with the selected signal reagent (e.g., chemiluminescent reagent, nitro-blue tetrazolium, or 5-bromo-4-chloro-3-indolyl phosphate.

Plaque Assay. The stably transfected E1A/E1B packaging cell clones are further characterized by adenoviral plaque assay. Plaques are monitored at 3, 7, 10, 14 days post-infection and can be observed with the unaided eye. For initial characterization, neutral red staining or standard brightfield microscopy may also be utilized. It is recognized that plaquing efficiencies of different recombinant adenoviral vectors may vary. Those packaging cell lines with plaque efficiencies of greater than 50% of that observed using 293 cells are preferred for the production of biological grade recombinant adenoviral vector stocks. Fluorescent Focus Assay (FFA) can alternatively be used. While FFA can be performed earlier (i.e., within 2 days), this method requires more expensive reagents. A flow cytometric assay, as described in Weaver et al. (*Methods* 2000 July; 21 (3): 297–312), may alternatively be used. The results from FFA, plaque assay, and flow cytometry are considered equivalent (Adenovirus Methods and Protocols, supra).

Viral Late Protein Expression in E1A/E1B Packaging Cell Lines. The E1A/E1B packaging cell lines are screened for the rate and production of viral late protein expression using a recombinant replication defective vector. Sufficient expression of functional E1A and E1B proteins by the packaging cell lines is thereby confirmed. Infected cells (M.O.I. of 5) are harvested 48 hours after infection into 15 ml centrifuge tubes and lysed in culture medium by 3 freeze-thaw cycles. The level of late protein accumulation is detected by immunoblotting with antibody directed against the adenovirus capsid. Hexon, penton and fiber proteins may be quantified and compared against similarly infected 293 cells. Mock infected E1A/E1B packaging cells and 293 cells are used as controls. Western blotting detection regents are commercially available (e.g. Amersham) and antibodies may similarly be obtained. (Adenovirus Methods, supra)

Kinetics of Virus Production. The kinetics of viral production using the E1A/E1B packaging cell lines may be evaluated using a replication deficient Ad vector expressing a β-gal transgene. Non-transduced A549 (i.e., native) cells are used as a control. Focus forming units are measured from harvested infected cells at 0, 15, 30, 45, 60, 75 hours post infection.

Isolation of Viral Lystates. Generally, viral lysates isolated from packaging cells are cleared by centrifugation and crude supernatants layered onto CsCl cushions and centrifuged at 32,000 rpm for 1 hour at 17° C. The collected bands are dialyzed four times at 4° C. with a final dialysis in TD buffer containing 17% glycerol. The resultant viral stocks are stored at −80 C. Such protocols are well known in the art (Graham and Prevec (1991) Methods in Molecular Biology, Vol. 7, Gene Transfer and Expression: Protocols).

RCA Detection Assay. An RCA study is done to compare the cells with traditional 293 and PerC6 cells (Gao et al., 2000, Hum Gene Thera 11:213; Murakami et al., 2002, Hum Gene Thera 13:909; Kim et al., 2001, Exp Mol Med 33:145). Different cells are used to passage a purified AdGFP or AdGM-CSF virus stock for up to 20 passages. Large-preparations of virus grown up in each cell line at different passages is purified. Naïve A549 cells were cultured in complete medium including DMEM/High, 10% fetal bovine serum, 1% glutamine and 1% Pen-Strep. Different amounts of viruses, about $10^8$ to $10^{13}$ PFU depending upon the cells, are used to infect A549 cells at an M.O.I of 2000. After six days, the cells are freeze-thawed and 10% of the lysate is used to infect new A549 cells for up to two weeks to evaluate potential CPE. Cell lysates derived from CPE assays are subjected to PCR verification for E1 region DNA. The frequency of RCA appearance is calculated accordingly.

Transduction: Ad-E1A and E1B genes were introduced into A549 cells by infecting the cells with MLV-E1A and MLV-E1B viruses by spinoculation. $1.5 \times 10^5$ cells were resuspended in 1 ml of E1AiE1B viral supernatants and 8 μl/ml of polybrene. The cell and virus mixture was then centrifuged at 3400 rpm at 34 C for 4 hours. To ensure optimal E1A/E1B ratios, three different E1A/E1B viral ratios (25% E1A/75% E1B, 50% E1A/50% E1B, 75% E1A/25% E1B) were used in spinoculation. MLV-GFP virus was included as a control for monitoring viral transduction efficiency. After spinoculation, the three populations were resuspended with complete medium, transferred into 6-well plates and incubated in 5% incubator at 37 C for 8 days.

Cloning: The three populations were dilution cloned on 10-cm dishes. After 18 days in culture, there were definite differences between the three populations. The 50/50 population had the fewest number of surviving "healthy" clones, while the population with 75% E1A/25% E1B had the most. Clones from all three populations were picked and transferred into 96-well plates, with duplicate plates made. These were grown for 5 days to allow cell expansion.

Functional Screen: One set of 96-well plates was infected with adenovirus to determine the ability of each clone to amplify adenovirus. To do so, each clone was infected with E1 deficient Ad-GFP virus at M.O.I. 10 at 100 μl/well for 48 hours. The cells were freeze/thawed 3× to release viral particles. These lysates were used to infect HuH7 cells. After 3-day infection, HuH7 cells were harvested and analyzed by FACS to evaluate for GFP expression. The clones whose supernatants gave high GFP expression in HuH7 cells were considered to be E1A/E1B-positive packaging clones. The data is shown in Table 1A. Those clones that transduced the HuH7 cells to the greatest extent were expanded and titered in the plaque assay.

Plaque Assay: In order to evaluate E1-complementary cells, the E1A deleted GFP virus was used to do functional test on the cells via virus yield assay. This virus replicates in the E1-expressing cells but not the parental or E1-negative cells. By comparing virus production from each clone, the E1-producing cells can be evaluated quantitatively for their support on viral replication. The test clones were infected with the E1A deleted Ad-GFP at M.O.I 5 for 4 hrs, refed with fresh media and incubated for 72 hr. Cells and media were harvested together, and subjected to 3 rounds of freeze/thaw. Serial dilutions were done in serum-free media and assayed on 293 cells which had been plated 24 hr earlier on $0.5 \times 10^6$ cells/well/4 ml media on 6-well plates. Incubate for 3–4 hrs. The samples were aspirated and 4 ml agarose (0.8% agarose in complete medium) applied as an overlay to each well. The plates were left at room temperature to solidify and incubate for plaque development. Table 1b shows the titers obtained.

TABLE 1

Identification of E1A/E1B complementing clones.

| Clones | A. Functional Screen* | B. Plaque Titers (pfu) × 1e5/ml** |
|---|---|---|
| A549 | 5.50% | 0.0 |
| Cl. 51 (50/50) | 91% | 6.0 |
| Cl. 54 (50/50) | 64.50% | 4.0 |
| Cl. 58 (50/50) | 66.80% | 7.5 |
| Cl. 100 (50/50) | 49.30% | 1.0 |
| Cl. 110 (50/50) | 61.90% | 6.0 |
| Cl. 122 (50/50) | 68.40% | 2.0 |
| Cl. 125 (50/50) | 54.70% | 2.8 |
| Cl. 139 (50/50) | 77.60% | 3.7 |
| Cl. 143 (50/50) | 65.90% | 4.0 |
| Cl. 40 (50/50) | 46% | 0.0 |
| Cl. 3 (25/75) | 61% | 1.0 |
| Cl. 9 (25/75) | 68.40% | 0.2 |
| Cl. 4 (25/75) | 54.40% | 0.0 |
| Cl. 33 (25/75) | 80.40% | 0.7 |
| Cl. 41 (25/75) | 69% | 1.0 |
| Cl. 42 (25/75) | 53% | 0.0 |
| 293 AAV | 99% | 2 × 10e7 |

*HuH7 were infected with adeno-GFP supernatants from clones to look for amplification as initial screen.
**Titers were determined by plaque assay as described in text.

Production of Oncolytic Virus Using Cell Lines Derived Form E1A/E1B Complementing Clones.

Two E1A/E1B clones (Clone 51 and 139), 293 cells and A549 cells were grown and infected with 4 oncolytic adenoviruses (CG8900, CG8840, OV945 and OV1025) for 3–4 hrs at an M.O.I. of 2. After 72 hrs the supernatant was harvested and used to infect 293 cells at different dilutions in a standard plaque assay. Infection was allowed to proceed for 4 hrs, and then the cells were cultured in agarose medium for 8–11 days. The results are shown in Table 2, below. CG8900, CG8840, OV945 and OV1024 are replication competent adenoviral vectors comprising cell type specific transcriptional regulatory elements controlling E1A and E1B.

TABLE 2

Oncolytic Virus Infection of A549, 293 and E1A/E1B Complementing Cell Lines.

| Virus Yield (Pfu/ml) | CG8900 | (Pfu/cell) CG8840 | OV945 | OV1025 |
|---|---|---|---|---|
| A549 | 1.20E+03 | 8.00E+01 | 1.20E+03 | 2.40E+03 |
| 293AAV | 2.80E+03 | 2.80E+03 | 4.00E+03 | 4.80E+03 |
| Cl.51 | 4.00E+04 | 3.20E+04 | 1.20E+04 | 4.00E+03 |
| Cl.139 | 1.60E+04 | 4.00E+03 | 8.00E+03 | 1.80E+04 |

The invention is not to be limited in scope by the recombinant expression vectors and cell lines exemplified, which are intended as illustrations of one aspect of the invention. It is to be understood that the above detailed examples and described embodiments are intended to illustrate and not limit the scope of the invention. Other aspects, advantages and modifications within the scope of the invention will be apparent to those skilled in the art to which the invention pertains.

What is claimed is:

1. A system comprising an adenoviral vector substantially free of wild type RCA and a packaging cell line permissive for replication of an E1A/E1B deficient adenovirus vector, wherein said packaging line comprises an adenovirus E1A coding sequence and an adenovirus E1B coding sequence operably linked to a promoter that lacks substantial sequence identity with a native adenovirus E1A or E1B promoter, and wherein said adenovirus E1A coding sequence and said adenovirus E1B coding sequence are stably integrated into said cell line and are operably linked to different heterologous promoters.

2. The system of claim 1, wherein said adenovirus E1A coding sequence and said adenovirus E1B coding sequence are stably integrated at different sites in said packaging line.

3. The system of claim 1, wherein said packaging line is a human cell line.

4. The system of claim 1, wherein the promoter in said packaging line that lacks substantial sequence identity with a native adenovirus E1A or E1B promoter is a retrovirus promoter.

5. The system of claim 1, wherein the adenovirus E1A coding sequence in said packaging line comprises the sequence set forth in SEQ ID NO:1.

6. The system claim 1, wherein the adenovirus E1B coding sequence in said packaging line comprises the sequence set forth in SEQ ID NO:4.

7. The system according to claim 1, wherein said packaging line comprises a first expression vector and a second expression vector stably integrated into the genome of said packaging line, wherein said first vector comprises adenovirus E1A coding sequences, operatively linked to a non-adenoviral heterologous promoter, and said second vector comprises adenovirus E1B coding sequences operatively linked to a non-gadenoviral heterologous promoter.

8. The system according to claim 1, wherein said vector is replication competent.

9. The system according to claim 8, wherein said replication competent vector is a chimeric vector comprised of sequences derived from more than one serotype.

10. The system according to claim 1, wherein said vector is replication defective.

11. The system of claim 3, wherein said packaging line is selected from the group consisting of A549 cells permissive for adenovirus replication PC-3 cells or primary cells permissive for adenovirus production.

12. The system according to claim 7, wherein said first expression vector is a retroviral expression vector.

13. The system according to claim 7, wherein said first and second expression vectors are retroviral expression vectors.

14. A system comprising an adenoviral vector substantially free of wild type RCA and a packaging cell line permissive for replication of an E1A/E1B deficient adenovirus vector, wherein said packaging line comprises an adenovirus E1A coding sequence and an adenovirus E1B coding sequence operably linked to a promoter that lacks substantial sequence identity with a native adenovirus E1A or E1B promoter, and wherein said adenovirus E1A coding sequence and said adonovirus E1B coding sequence are stably integrated into said cell line and are operably linked to identical promoters.

15. The system of claim 14, wherein said adenovirus E1A coding sequence and said adenovirus E1B coding sequence are stably integrated at different sites in said packaging line.

16. The system of claim 14, wherein said packaging line is a human cell line.

17. The system of claim 14, wherein the promoter in said packaging line that lacks substantial sequence identity with a native adenovirus E1A or E1B promoter is a retrovirus promoter.

18. The system of claim 14, wherein the adenovirus E1A coding sequence in said packaging line comprises the sequence set forth in SEQ ID NO:1.

19. The system of claim 14, wherein the adenovirus E1B coding sequence in said packaging line comprises the sequence set forth in SEQ ID NO:4.

20. The system according to claim 14, wherein said adenoviral vector is replication competent.

21. The system according to claim 14, wherein said replication competent adenoviral vector is a chimeric vector comprised of sequences derived from more than one serotype.

22. The system according to claim 14, wherein said adenoviral vector is replication defective.

23. The system of claim 16, wherein said packaging line is selected from the group consisting of A549 cells permissive for adenovirus replication PC-3 cells or primary cells permissive for adenovirus production.

* * * * *